United States Patent [19]

Douglas et al.

[11] 4,439,278
[45] Mar. 27, 1984

[54] PROCESS INHIBITOR FOR READILY POLYMERIZABLE ETHYLENICALLY UNSATURATED AROMATIC COMPOUNDS

[75] Inventors: Ted L. Douglas; Ambrose J. Clonce; Glenn C. Jones, all of Kingsport, Tenn.

[73] Assignee: Eastman Kodak Company, Rochester, N.Y.

[21] Appl. No.: 489,678

[22] Filed: Apr. 28, 1983

Related U.S. Application Data

[63] Continuation-in-part of Ser. No. 390,489, Jun. 21, 1982, Pat. No. 4,389,285.

[51] Int. Cl.³ ............................ C07C 7/20; B01D 3/34
[52] U.S. Cl. .......................................... 203/9; 203/60; 203/61; 203/65; 203/91; 585/5; 585/800; 585/860; 585/866
[58] Field of Search ................................ 203/6–9, 203/65, 60, 61, 38, 57, 91; 585/4, 5, 800, 860, 863, 866

[56] References Cited

U.S. PATENT DOCUMENTS

| | | | |
|---|---|---|---|
| 2,826,581 | 3/1958 | Mahan et al. | 585/5 |
| 3,407,240 | 10/1968 | Sakashita et al. | 585/5 |
| 3,551,507 | 12/1970 | Sakuragi et al. | 203/9 |
| 3,988,212 | 10/1976 | Watson | 203/9 |
| 4,105,506 | 8/1978 | Watson | 203/9 |
| 4,272,344 | 6/1981 | Watson | 203/9 |
| 4,376,678 | 3/1983 | Partos | 203/9 |
| 4,389,285 | 6/1983 | Douglas et al. | 203/9 |

FOREIGN PATENT DOCUMENTS

39-1817  2/1964  Japan.

Primary Examiner—Wilbur L. Bascomb, Jr.
Attorney, Agent, or Firm—David E. Cotey; Daniel B. Reece, III

[57] ABSTRACT

The present invention provides an improvement in methods for preparing and processing ethylenically unsaturated aromatic monomer. The improvement comprises employing 3,5-dinitrosalicylic acid or a derivative or isomer thereof as a process inhibitor. The process inhibitor is present in a concentration of about 50 to 3000 ppm, preferably about 250 to 2,000 ppm, and most preferably about 500 to 1,000 ppm.

8 Claims, No Drawings

PROCESS INHIBITOR FOR READILY POLYMERIZABLE ETHYLENICALLY UNSATURATED AROMATIC COMPOUNDS

DESCRIPTION

This application is a continuation-in-part of U.S. application Ser. No. 390,489, filed June 21, 1982 and now U.S. Pat. No. 4,389,285, entitled "Process Inhibitor for Readily Polymerizable Ethylenically Unsaturated Aromatic Compounds" (Inventors: T. L. Douglas, A. J. Clonce, Jr., and G. C. Jones).

BACKGROUND OF THE INVENTION

Readily polymerizable ethylenically unsaturated aromatic compounds, such as styrene monomer, are important chemicals of commerce, the current production of styrene monomer being about 10 billion pounds per year. Essentially all of the styrene currently produced is made by processes involving the dehydrogenation of ethylbenzene. Such processes typically include a styrene distillation step wherein the distillation is conducted under a nitrogen atmosphere at a temperature of about 110° C. and a pressure in the range of about 100 to 190 mm Hg. Under these conditions, the reactivity of styrene necessitates the use of a relatively large amount of process inhibitor to prevent polymerization. Likewise, current processes for the production of other ethylenically unsaturated aromatic compounds, such as α-methylstyrene, vinyl toluene, vinyl naphthalene, divinylbenzene, etc., commonly employ vacuum distillation techniques and require the use of a process inhibitor.

The industry currently employs 4,6-dinitro-orthocresol (DNOC) as a process inhibitor. However, DNOC is a highly toxic process inhibitor. The toxicity of DNOC raises exposure concerns with regard to monomer production, the preparation of DNOC stock solutions, and the ill effects of accidental spills. Therefore, there exists a need in the industry for a process inhibitor to replace the highly toxic DNOC.

It has now been found that 3,5-dinitrosalicylic acid (3,5-dinitro-2-hydroxybenzoic acid; DNSA) and certain derivatives and isomers thereof can be safely employed as process inhibitors for readily polymerizable ethylenically unsaturated aromatic compounds. DNSA exhibits an effectiveness equal to or greater than DNOC and has been shown to be much less toxic than DNOC. The claimed derivatives and isomers of DNSA have also been found to be effective process inhibitors.

Foord et al. disclose in *J. Chem. Soc.*, 1940, pp. 48–56, the effectiveness of quinones as a class of styrene polymerization inhibitors. The reference further discloses the usefulness as polymerization retarders of aromatic compounds having a number of various substituents, including quinonoid, nitro, phenolic hydroxy, amino, and nitroso groups. However, the reference does not disclose the significantly greater inhibitory effect of DNSA over that observed for the other members of the described class of "retarders".

Japanese Pat. No. 39-1817(1964) discloses stabilizers for use in conjunction with unsaturated polyester resins. The patent discloses that suitable stabilizers are nitro compounds which are represented by formula I. It is further disclosed that 3,5-dinitrosalicylic acid (DNSA) is a suitable stabilizer (see Example 5 of the reference). However, the disclosure of the reference relates solely to the curing of unsaturated polyester resins. Such a system relates solely to a copolymerization process involving different reaction rates from those encountered in the polymerization of styrene, which is a homopolymerization process and to which the present invention relates. In addition, the "stabilizers" of the Japanese patent are utilized in the unsaturated polyester resin in a storage environment, whereas in the present invention, DNSA and the claimed derivatives and isomers thereof are utilized as process inhibitors. In addition, the improved effectiveness of DNSA and certain derivatives and isomers thereof as styrene polymerization inhibitors is not disclosed.

Thus, the improved effectiveness of DNSA and certain derivatives and isomers thereof as polymerization inhibitors was neither disclosed nor suggested by the prior art. Furthermore, the art did not recognize the toxicity problems posed by certain previously known inhibitors and certainly did not propose the use of DNSA and derivatives and isomers thereof as a means for solving those problems.

SUMMARY OF THE INVENTION

The present invention provides an improvement in processes for the preparation of readily polymerizable ethylenically unsaturated aromatic compounds. The improvement comprises employing 3,5-dinitrosalicylic acid and certain derivatives and isomers thereof as process inhibitors. The derivatives and isomers of DNSA may be selected from lower alkyl esters of 3,5-dinitrosalicylic acid, phenyl-3,5-dinitrosalicylate, 3,5-dinitro-4-hydroxybenzoic acid and lower alkyl esters thereof, and mixtures of the foregoing.

DETAILED DESCRIPTION OF THE INVENTION

The present invention relates to the use of 3,5-dinitrosalicylic acid and derivatives and isomers thereof as process inhibitors in the preparation of readily polymerizable ethylenically unsaturated aromatic compounds. As used herein, the term "process inhibitor" refers to a polymerization inhibitor which is employed during the preparation and processing of the monomer. Process inhibitors can be distinguished from product inhibitors, which are combined with the monomer in order to inhibit polymerization during storage and handling.

According to the process of the present invention, 3,5-dinitrosalicylic acid (DNSA) is employed as a process inhibitor during the preparation and processing of certain monomeric substances. DNSA is a well-known chemical compound whose preparation is also well known in the art. DNSA is available commercially from a number of sources.

Also according to the process of the present invention, certain derivatives and isomers of DNSA may be employed as process inhibitors. These derivatives and isomers include the lower alkyl esters of 3,5-dinitrosalicylic acid, phenyl-3,5-dinitrosalicylate, 3,5-dinitro-4-hydroxybenzoic acid, lower alkyl esters of 3,5-dinitro-4-hydroxybenzoic acid, and mixtures thereof. The term "lower alkyl" as used in this context signifies moieties containing up to about four carbon atoms. Such moieties include methyl, ethyl, n-propyl, isopropyl, n-butyl, isobutyl, etc. Especially preferred as a lower alkyl ester of DNSA is methyl-3,5-dinitrosalicylate. In addition to the lower alkyl esters, aryl esters of DNSA may also be employed. A particularly preferred aryl ester is phenyl-3,5-dinitrosalicylate. Also useful are isomers of DNSA, such as 3,5-dinitro-4-hydroxybenzoic acid and lower alkyl esters thereof.

Each of these derivatives and isomers can be prepared by known procedures involving the nitration of the appropriate salicylic acid derivative. For example, methyl-3,5-dinitrosalicylate is prepared by the nitration of methylsalicylate, and 3,5-dinitro-4-hydroxybenzoic acid is prepared by the nitration of 4-hydroxybenzoic acid. The other disclosed derivatives and isomers can be prepared in a similar manner.

Certain of these derivatives and isomers, such as the methyl and phenyl esters of DNSA, exhibit about the same effectiveness as process inhibitors, on a molar basis, as does DNSA. In addition, the esters tend to exhibit improved solubility in styrene, which is a desirable feature for a process inhibitor.

The present process is applicable to readily polymerizable ethylenically unsaturated aromatic compounds. Such compounds include styrene, α-methylstyrene, vinyl toluene, vinyl naphthalene, divinylbenzene, etc. Compounds preferred for use in the process of the present invention include styrene and α-methylstyrene, with styrene being particularly preferred. While portions of the present specification refer specifically to styrene as an illustrative member of this class of compounds, it is to be understood that this specification applies to all members of the described class of readily polymerizable ethylenically unsaturated aromatic compounds.

As stated above, during the latter stages of current processes for the production of ethylenically unsaturated aromatic compounds, the crude monomer is typically subjected to vacuum distillation in order to remove excess reactants and other volatile aromatic impurities. In accordance with the process of the present invention, DNSA or a suitable derivative or isomer thereof is employed as a process inhibitor during the preparation of the monomer and especially during the distillation step, which is when polymerization is most likely to occur. Whenever DNSA is referred to as a process inhibitor in this specification, it will be understood that the disclosed derivatives and isomers of DNSA are also suitable for use in a like manner.

The DNSA, or derivative or isomer thereof, can be supplied to the process in a variety of ways. It can be introduced at the beginning of the reaction, for example, a dehydrogenation reaction in the case of certain of the compounds (such as styrene), and be present in the reaction stream from the initiation of the reaction through the distillation of the crude monomer. Alternatively, the DNSA can be provided to the vessel in which the distillation of the crude monomer occurs. In preferred embodiments, the major portion of the DNSA is provided to the reaction system at the beginning of the reaction for the production of monomer, and an additional minor amount of DNSA is fed near the top of the apparatus for the distillation of the crude monomer and is allowed to fall through the distillation apparatus in a direction countercurrent to the direction of flow of the impurities being distilled from the crude monomer. Such impurities often include the initial reactant, such as ethylbenzene in the case of the production of styrene. Thus, in such a preferred scheme, the total amount of DNSA process inhibitor present in the system is available for intimate contact with the monomer in the distilland. Regardless of the manner in which the DNSA is provided to the reaction system, the DNSA is typically removed from the system in the final distillation wherein crude monomer is taken overhead and the remaining impurities and the DNSA inhibitor are taken off as bottoms from the column.

The DNSA or derivative or isomer thereof is provided to the reaction system in an amount which is sufficient to effect the inhibition of polymerization. Typically, the DNSA will be present in an amount of about 50 to 3,000 ppm, based upon the weight of DNSA per total weight of reactants and products present in the distilland. Preferably, the DNSA is present in a concentration of about 250 to 2,000 ppm, with a concentration of about 500 to 1,000 ppm being especially preferred.

DNSA and the disclosed derivatives and isomers thereof can be provided to the styrene preparation process either directly or as a stock solution. DNSA and its derivatives and isomers are sufficiently soluble in suitable carrier solvents to allow the preparation of such a stock solution. Suitable carrier solvents include alpha-methylbenzyl alcohol, mixtures of alpha-methylbenzyl alcohol and acetophenone (e.g., a 15:85 acetophenone:alpha-methylbenzyl alcohol blend), water, etc. The use of stock solutions of process inhibitors is well known in the art and is a wide-spread practice.

Additional inhibitors may also be present during the process of the present invention. For example, product inhibitors, such as t-butylcatechol, may also be present during the preparation and/or distillation of the crude monomer.

The invention will be further illustrated by the following Examples although it will be understood that these Examples are included merely for purposes of illustration and are not intended to limit the scope of the invention.

EXAMPLE 1

This Example illustrates the improved inhibiting effect provided by DNSA.

In each run of the present Example, the indicated amount of DNSA was added to 500 ml of commercial styrene monomer containing 50 ppm t-butylcatechol (TBC). The inhibited styrene was refluxed under sufficient vacuum to maintain the temperature at 100° C. After three hours of reflux and after six hours of reflux, 10-gram samples were contacted with 15 ml of methyl alcohol, causing any polymer present in the sample to precipitate. The polymer was collected, dried at 210° C., and weighed. The results are listed in Table I.

TABLE I

| DNSA Concentration | Percent Polymer Formation | |
|---|---|---|
| (ppm) | 3 Hrs. Reflux | 6 Hrs. Reflux |
| 250 | 0.90 | 5.9 |
| 500 | 0.30 | 1.5 |
| 1000 | 0.10 | 0.3 |
| 1500 | 0.04 | 0.12 |
| 2000 | 0.00 | 0.06 |

COMPARATIVE EXAMPLE 1

Example 1 was repeated except that the DNSA was replaced with 4,6-dinitro-ortho-cresol (DNOC) which was obtained commercially from Blue Spruce International. The results are given in Table II.

TABLE II

| DNOC Concentration | Percent Polymer Formation | |
|---|---|---|
| (ppm) | 3 Hrs. Reflux | 6 Hrs. Reflux |
| 250 | 1.9 | 8.3 |
| 500 | 0.75 | 2.2 |
| 1000 | 0.30 | 0.90 |

TABLE II-continued

| DNOC Concentration (ppm) | Percent Polymer Formation | |
|---|---|---|
| | 3 Hrs. Reflux | 6 Hrs. Reflux |
| 1500 | 0.14 | 0.24 |
| 2000 | 0.07 | 0.04 |

It can be seen from a comparison of the data of Tables I and II that DNSA is far more effective as a process inhibitor than is DNOC. In virtually every case, the percent polymer formation for DNSA is approximately half or less than that for DNOC. In addition, DNSA is much less toxic than DNOC. Therefore, its use as a process inhibitor is far more safe and effective than is the use of DNOC.

EXAMPLE 2

Example 1 was repeated except that 500 ppm DNSA was added to distilled styrene and to distilled styrene to which 50 ppm t-butylcatechol had been added. The results are given in Table III.

TABLE III

| Monomer | Percent Polymer Formation | |
|---|---|---|
| | 3 Hrs. Reflux | 6 Hrs. Reflux |
| distilled styrene | 0.06 | 0.72 |
| distilled styrene + 50 ppm TBC | 0.09 | 0.80 |

COMPARATIVE EXAMPLE 2

Example 2 was repeated except that the DNSA was replaced with DNOC. The results are given in Table IV.

TABLE IV

| Monomer | Percent Polymer Formation | |
|---|---|---|
| | 3 Hrs. Reflux | 6 Hrs. Reflux |
| distilled styrene | 0.39 | 1.7 |
| distilled styrene + 50 ppm TBC | 0.28 | 1.7 |

Again, Tables III and IV demonstrate the improved effectiveness of DNSA as a styrene process inhibitor both in the presence and absence of TBC as product inhibitor.

EXAMPLE 3

This Example illustrates the preparation of 3,5-dinitro-4-hydroxybenzoic acid.

A mixture of 4-hydroxybenzoic acid (1.4 g; 0.01 mole) and concentrated sulfuric acid (7.0 g) was stirred until complete dissolution was achieved. To this solution there was slowly added, with cooling, a mixture of 1.25 g (0.2 mole) of concentrated (98%) nitric acid in 3.0 g of concentrated sulfuric acid. The mixture was allowed to stand for two hours. The mixture was then poured into ice water. The solid product was removed by filtration and was dried and weighed. A yield of 1.9 g (83%) was obtained. The product exhibited a melting point of 210°–238° C. The product was recrystallized from 200 ml of water, yielding 1.1 g of product having a melting point of 235°–245° C. The product was analyzed by NMR spectroscopy.

The effectiveness of 3,5-dinitro-4-hydroxybenzoic acid as a process inhibitor was determined as in Example 1. The results are given in Table V.

EXAMPLE 4

This Example illustrates the preparation of methyl-3,5-dinitrosalicylate and its effectiveness as a process inhibitor.

Methylsalicylate (15.2 g; 0.1 mole) was dissolved in about 50 ml of 96% sulfuric acid. A mixture of 15 grams (0.23 moles) of nitric acid in 94 grams sulfuric acid was added dropwise to the methylsalicylate solution. Due to the exothermicity of the reaction, the addition was conducted over a period of time of about two hours and at a temperature less than about 25° C. After the addition of all of the acid mixture, the reaction mixture was stirred for an additional hour. The reaction mixture was then drowned with about 275 grams of ice, thereby cooling the reaction mixture to about 5° C. The product was filtered from the reaction mixture and was washed with about 200 ml H$_2$O. A lightly colored solid was obtained. The product was oven-dried at 40° C. under a vacuum. There was obtained 23 grams of product having a melting point of 126°–127° C.

The effectiveness of the product as a process inhibitor was evaluated as in Example 1. The results are given in Table V below.

EXAMPLE 5

This Example illustrates the preparation of phenyl-3,5-dinitrosalicylate and its usefulness as a process inhibitor for styrene.

3,5-Dinitrosalicylic acid (114 grams; 0.5 mole) was mixed with 100 grams (1.06 mole) of phenol and about 300 ml of toluene, and the mixture was heated to about 110° C. Phosphorus oxychloride (POCl$_3$: 91.2 g; 0.61 mole) was added dropwise over a period of about an hour at a temperature of about 100° C. The resulting mixture was stirred overnight at a temperature of about 100° C. Thereafter, 100 ml of water was added at 70° to 100° C., and 200 ml of toluene was subsequently added. The resulting mixture comprising a solid phase, an aqueous phase, and an organic phase was subjected to further mixing. The solids were filtered, dried, and weighed, giving a yield of 110 grams. The filtrate was separated, and the light brown aqueous phase was discarded, while the organic phase was cooled slowly to crystallize additional product. This additional product was dried and weighed, yielding an additional 21 grams.

The effectiveness of the product phenyl-3,5-dinitrosalicylate as a styrene process inhibitor was evaluated as in Example 1, and the results are given in Table V.

COMPARATIVE EXAMPLE 3

For purposes of comparison, commercial styrene containing 50 ppm of the product inhibitor t-butylcatechol (TBC) was refluxed for three hours and for six hours and the percent polymer formation was determined. The results are given in Table V below.

TABLE V

| Run | Inhibitor Concentration (ppm) | Percent Polymer Formation | |
|---|---|---|---|
| | | 3 Hrs. Reflux | 6 Hrs. Reflux |
| Comp. Ex. 3 | — | 17.0 | — |
| Ex. 3 | 500 | 0.42 | 2.6 |
| Ex. 4 | 500 | 0.82 | 1.5 |
| Ex. 5 | 500 | 1.6 | 4.2 |

It can be seen from a review of the results of Table V that the DNSA isomer and the DNSA derivatives illustrated in Examples 3 through 5 are effective as styrene polymerization inhibitors.

The invention has been described in detail with particular reference to preferred embodiments thereof, but it will be understood that variations and modifications can be effected within the spirit and scope of the invention.

We claim:

1. In processes for the preparation of readily polymerizable ethylenically unsaturated aromatic compounds, the improvement which comprises employing a substance selected from lower alkyl esters of 3,5-dinitrosalicyclic acid, phenyl-3,5-dinitrosalicylate, 3,5-dinitro-4-hydroxybenzoic acid, lower alkyl esters of 3,5-dinitro-4-hydroxybenzoic acid, and mixtures thereof as a process inhibitor.

2. The process of claim 1 wherein said process inhibitor comprises methyl-3,5-dinitrosalicylate.

3. The process of claim 1 wherein said process inhibitor is present in a concentration of about 50 to 3,000 ppm.

4. The process of claim 1 wherein said process inhibitor is present in a concentration of about 250 to 2,000 ppm.

5. The process of claim 1 wherein said readily polymerizable ethylenically unsaturated aromatic compound is selected from styrene, α-methylstyrene, vinyl toluene, vinyl naphthalene, divinylbenzene, and mixtures thereof.

6. The process of claim 5 wherein said readily polymerizable ethylenically unsaturated aromatic compound comprises styrene.

7. In a process for the preparation of styrene which includes a distillation step at elevated temperature and/or reduced pressure, the improvement which comprises providing a substance selected from methyl-3,5-dinitrosalicylate, phenyl-3,5-dinitrosalicylate, 3,5-dinitro-4-hydroxybenzoic acid, and mixtures thereof to the distilland in a concentration of about 250 to 2,000 ppm.

8. The process of claim 7 wherein said process inhibitor is present in the distilland in a concentration of about 500 to 1,000 ppm.

* * * * *